(12) United States Patent
von Hatten (10) Patent No.: US 11,733,147 B2
(45) Date of Patent: Aug. 22, 2023

(54) FLOW CELLS

(71) Applicant: ILLUMINA CAMBRIDGE LIMITED, Cambridge (GB)

(72) Inventor: Xavier von Hatten, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 836 days.

(21) Appl. No.: 16/522,345

(22) Filed: Jul. 25, 2019

(65) Prior Publication Data

US 2020/0041401 A1 Feb. 6, 2020

Related U.S. Application Data

(60) Provisional application No. 62/715,177, filed on Aug. 6, 2018.

(51) Int. Cl.
*G01N 15/14* (2006.01)
*C12Q 1/68* (2018.01)
*C12Q 1/6869* (2018.01)

(52) U.S. Cl.
CPC ........... *G01N 15/14* (2013.01); *C12Q 1/6869* (2013.01)

(58) Field of Classification Search
CPC .............................. C12Q 1/6869; G01N 15/14
See application file for complete search history.

(56) References Cited

U.S. PATENT DOCUMENTS

| | | | |
|---|---|---|---|
| 8,778,849 B2 * | 7/2014 | Bowen | B01J 19/0046 506/30 |
| 2004/0086870 A1 | 5/2004 | Tyvoll et al. | |
| 2005/0214471 A1 | 9/2005 | Theobald et al. | |
| 2010/0015805 A1 | 1/2010 | Mayer et al. | |
| 2011/0183123 A1 | 7/2011 | Buck et al. | |
| 2013/0244249 A1 | 9/2013 | Jiang et al. | |
| 2014/0243224 A1 * | 8/2014 | Barnard | C12Q 1/6837 506/26 |
| 2014/0311966 A1 | 10/2014 | Buck et al. | |
| 2015/0240300 A1 | 8/2015 | Ansari et al. | |

(Continued)

FOREIGN PATENT DOCUMENTS

| | | |
|---|---|---|
| CN | 101400993 A | 4/2009 |
| CN | 101492503 A | 7/2009 |
| RU | 2574249 C2 | 2/2016 |

(Continued)

OTHER PUBLICATIONS

Theobald, et al. "Controlling Molecular Deposition and Layer Structure with Supramolecular Survace Assemblies", Nature, vol. 424, Aug. 28, 2003, 1029-1031.

(Continued)

*Primary Examiner* — Jezia Riley
(74) *Attorney, Agent, or Firm* — Dierker & Kavanaugh, P.C.

(57) ABSTRACT

In an example, a flow cell includes a substrate, a selectively removable porous molecular network on the substrate and defining exposed substrate regions, and sequencing surface chemistry on at least some of the exposed regions. The sequencing surface chemistry is selected from the group consisting of i) an activated pad, a polymer layer attached to the activated pad, and a primer attached to the polymer layer; or ii) a nanostructure and an enzyme attached to the nanostructure.

4 Claims, 3 Drawing Sheets

(56) References Cited

U.S. PATENT DOCUMENTS

2016/0122816 A1* 5/2016 Brown .................. C08F 20/60
526/306
2018/0037950 A1 2/2018 Gunderson et al.

FOREIGN PATENT DOCUMENTS

| WO | 2003/012390 | A2 | 2/2003 |
| WO | 2010/004280 | A1 | 1/2010 |
| WO | 2013/063382 | A2 | 5/2013 |
| WO | 2014/133905 | A1 | 9/2014 |
| WO | 2016/010975 | A2 | 1/2016 |
| WO | 2016/183218 | A1 | 11/2016 |
| WO | 2017/037078 | A1 | 3/2017 |
| WO | 2017/201198 | A1 | 11/2017 |

OTHER PUBLICATIONS

Kerfoot, J., et al., "The Growth and Fluorescence of Organic Monolayers and Heterostructures", Retrieved from Internet: URL:http://eprints.nottingham.ac.uk/50673/1/Thesis_Corrections_1.pdf, Jan. 1, 2008.

Madueno, R., et al., "Functionalizing hydrogen-bonded surface networks with self-assembled monolayers", Nature 454, 2008, 618-621.

* cited by examiner

| | |
|---|---|
| Applying a Porous Molecular Network to a Substrate to Define a Pattern of Exposed Substrate Regions | 102 |
| Activating the Exposed Substrate Regions to Form Activated Pads | 104 |
| Removing the Porous Molecular Network, whereby the Activated Pads Remain Intact and are Separated by Interstitial Substrate Regions | 106 |
| Applying a Respective Polymer Layer to Each of the Activated Pads | 108 |
| Grafting a Primer to Each of the Respective Polymer Layers | 110 |

Forming a Masked Substrate by Applying a Porous Molecular Network to a Surface of a Substrate Having Nanostructures Assembled thereon, whereby at least a Portion of Each Nanostructure Remain Exposed — 202

Exposing the Masked Substrate to an Enzyme Solution that is Inert to the Porous Molecular Network, thereby Selectively Attaching a Respective Enzyme to at least Some of the Exposed Portions of the Nanostructures — 204

FLOW CELLS

CROSS-REFERENCE TO RELATED APPLICATIONS

This application claims the benefit of U.S. Provisional Application Ser. No. 62/715,177, filed Aug. 6, 2018, the content of which is incorporated by reference herein in its entirety.

BACKGROUND

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. In some examples, the controlled reactions generate fluorescence, and thus an optical system may be used for detection. In other examples, the controlled reactions alter charge, conductivity, or some other electrical property, and thus an electronic system may be used for detection.

INTRODUCTION

A first aspect disclosed herein is a flow cell. The flow cell comprises a substrate; a selectively removable porous molecular network on the substrate and defining exposed substrate regions; and sequencing surface chemistry on at least some of the exposed regions, the surface chemistry selected from the group consisting of: i) an activated pad, a polymer layer attached to the activated pad, and a primer attached to the polymer layer; or ii) a nanostructure and an enzyme attached to the nanostructure.

In an example of the flow cell, the selectively removable porous molecular network is a planar supramolecular network of an amine and a di-imide. In one example, the amine is melamine or an analog thereof and wherein the di-imide is perylene tetracarboxylic di-imide or an analog thereof.

In an example of the flow cell, the surface chemistry is ii) the nanostructure and the enzyme attached to the nanostructure; and in ii): the nanostructure is a conductive channel including a material selected from the group consisting of a conductor and a semiconductor, and having a geometry selected from the group consisting of a tube, a wire, and a ribbon; and the enzyme is a polymerase. In one example, one polymerase is attached to one nanostructure. In one example, the nanostructure is electrically connected to two electrodes. In one example, the flow cell further comprises a tether attaching the polymerase to the nanostructure. In one example, the nanostructure is selected from the group consisting of a silicon nanowire and a carbon nanotube.

In an example of the flow cell, the surface chemistry is i) the activated layer, the polymer layer, and the primer; and in i) the polymer layer is:

wherein: $R^1$ is H or optionally substituted alkyl; $R^4$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol; $R^5$, $R_6$, and $R_8$ are each independently selected from the group consisting of H and optionally substituted alkyl; each of the —$(CH_2)_p$— can be optionally substituted; p is an integer in the range of 1 to 50; n is an integer in the range of 1 to 50,000; and m is an integer in the range of 1 to 100,000.

It is to be understood that any features of the flow cell disclosed herein may be combined together in any desirable manner and/or configuration.

A second aspect disclosed herein is a sequencing system. The sequencing system comprises a removable flow cell, including: a substrate; a selectively removable porous molecular network on the substrate and defining exposed substrate regions; a nanostructure attached to each of the exposed substrate regions; an enzyme attached to the at least some of the nanostructures; and input and output fluid ports; a receptacle to i) permanently house the removable flow cell or ii) receive the removable flow cell; and a fluidic system to selectively deliver a de-patterning reagent to the removable flow cell to remove the selectively removable porous molecular network from the substrate and a patterning reagent to the removable flow cell to apply a fresh selectively removable porous molecular network to the substrate.

In an example of the sequencing system, each of the nanostructures is a conductive channel including a material selected from the group consisting of a conductor and a semiconductor, and having a geometry selected from the group consisting of a tube, a wire, and a ribbon; and each of the nanostructures is individually electrically addressable.

In an example of the sequencing system, the fluidic system includes a cartridge receptacle to receive a reagent cartridge including at least the de-patterning reagent and the patterning reagent. In some examples, the sequencing system further comprises the reagent cartridge, where the reagent cartridge includes: a fluid storage system, including: a de-patterning reagent receptacle; the de-patterning reagent contained within the de-patterning reagent receptacle; a patterning reagent receptacle including two separate compartments; a first component of the patterning reagent contained within a first of the two separate compartments; and a second component of the patterning reagent contained within a second of the two separate compartments. In one example, the de-patterning reagent includes an oxidizing reagent; the first component of the patterning reagent is perylene tetracarboxylic di-imide or an analog thereof; and the second component of the patterning reagent is melamine or an analog thereof. In one example, the oxidizing reagent is selected from the group consisting of permanganates, perborates, halogens, perchlorates, and peroxides.

It is to be understood that any features of the sequencing system may be combined together in any desirable manner. Moreover, it is to be understood that any combination of features of the sequencing system and/or of the flow cell may be used together, and/or combined with any of the examples disclosed herein.

A third aspect disclosed herein is a method. The method comprises forming a masked substrate by applying a porous molecular network to a surface of a substrate having nanostructures positioned thereon, whereby at least a portion of each nanostructure remain exposed; and exposing the masked substrate to an enzyme solution that is inert to the porous molecular network, thereby selectively attaching a respective enzyme to at least some of the exposed portions of the nanostructures.

In an example of this method, the applying of the porous molecular network involves: heating a saturated mixture of perylene tetracarboxylic di-imide or an analog thereof and melamine or an analog thereof; depositing the saturated mixture on the substrate having nanowires attached thereto; and cooling the deposited saturated mixture.

It is to be understood that any features of this method may be combined together in any desirable manner. Moreover, it is to be understood that any combination of features of this method and/or of the sequencing system and/or of the flow cell may be used together, and/or combined with any of the examples disclosed herein.

A fourth aspect disclosed herein is another method. This method comprises applying a porous molecular network to a substrate to define a pattern of exposed substrate regions; activating the exposed substrate regions to form activated pads; removing the porous molecular network, whereby the activated pads remain intact and are separated by interstitial substrate regions; applying a respective polymer layer to each of the activated pads; and grafting a primer to each of the respective polymer layers.

In an example of this method, removing the porous molecular network involves exposing the porous molecular network to an oxidizing reagent.

In an example of this method, the applying of the porous molecular network involves: heating a saturated mixture of perylene tetracarboxylic di-imide or an analog thereof and melamine or an analog thereof; depositing the saturated mixture on the substrate having nanowires attached thereto; and cooling the deposited saturated mixture.

It is to be understood that any features of this method may be combined together in any desirable manner. Moreover, it is to be understood that any combination of features of this method and/or of the sequencing system and/or of the flow cell may be used together, and/or combined with any of the examples disclosed herein.

Still further, it is to be understood that any features of any of the methods and/or of any of the sequencing systems and/or of any of the flow cells may be combined together in any desirable manner, and/or may be combined with any of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

In the examples disclosed herein, patterning at the nanometer scale is enabled through the use of a porous molecular network. The porous molecular network self-assembles on a substrate surface and creates a pattern where i) portions of the underlying substrate or ii) nanostructures pre-disposed on the substrate are exposed. The highly hydrophobic porous molecular network covers at least substantially the remainder of the substrate surface, and thus creates a mask on the substrate surface. This mask may minimize, and in some instances even entirely prevents, subsequently deposited surface chemistry from attaching thereto, but does not prevent the subsequently deposited surface chemistry from attaching to i) the exposed portions of the underlying substrate or ii) the exposed nanostructures. As such, the porous molecular network functionalization of only the desired areas.

The porous molecular network is also readily removable from the substrate surface using mild conditions that do not deleteriously affect the applied surface chemistry.

In some examples disclosed herein, the porous molecular network may also remain on the substrate surface during a sequencing operation. In these examples, the highly hydrophobic porous molecular network may help to increase the interaction between introduced reagents and the surface chemistry.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

As used herein, the term "attached" refers to the state of two things being joined, fastened, adhered, connected or bound to each other. For example, a nucleic acid can be attached to a polymer coating by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions.

As used herein, the term "flow cell" is intended to mean a vessel having a chamber (i.e., flow channel) where a reaction can be carried out, an inlet for delivering reagent(s) to the chamber, and an outlet for removing reagent(s) from the chamber. In some examples, the chamber enables the detection of the reaction that occurs in the chamber. For example, the chamber/flow channel can include one or more transparent surfaces allowing for the optical detection of arrays, optically labeled molecules, or the like, at the depression. For another example, the chamber/flow channel can include electronic circuitry allowing for the detection of electrical signals.

The term "depositing," as used herein, refers to any suitable application technique, which may be manual or automated, and results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, screen printing, microcontact printing, ink-jet printing, or the like.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA).

As used herein, the "primer" is defined as a single stranded nucleic acid sequence (e.g., single strand DNA or single strand RNA). Some primers, which may be referred to as amplification primers, serve as a starting point for template amplification and cluster generation. Other primers, which may be referred to as sequencing primers, serve as a starting point for DNA or RNA synthesis. The 5' terminus, e.g., of the amplification primer may be modified to allow a coupling reaction with a functional group of a polymer coating. The primer length can be any number of bases long and can include a variety of non-natural nucleotides. In an example, the sequencing primer is a short strand, ranging from 10 to 60 bases, or from 20 to 40 bases.

The term "substrate" refers to a support upon which various components of the flow cell may be added. The support may be a wafer, a panel, a rectangular sheet, a die, or any other suitable configuration. The support is generally rigid and is insoluble in an aqueous liquid. The support may be inert to a chemistry that is used to modify the depressions. For example, a support can be inert to chemistry used to form the block copolymer, to attach the primer(s), etc. Examples of suitable supports will be described further below.

The term "surface chemistry," as used herein refers, in some aspects, to an activated pad, a polymer layer attached to the activated pad, and primer(s) attached to at least a portion of the polymer layer. In other aspects, the term "surface chemistry" refers to a nanostructure and an enzyme attached to the nanostructure.

Porous Molecular Network

In the examples disclosed herein, the porous molecular network is a planar supramolecular network of an amine and a di-imide. The selected amine and di-imide preferentially undergo heteromolecular hydrogen bonding over homomolecular hydrogen bonding. The following is an example of the heteromolecular hydrogen bonding between melamine and perylene tetra-carboxylic di-imide (PTCDI):

As depicted above, three hydrogen bonds are formed between these molecules. Melamine includes three functional units ($H_2N-C-N-C-NH_2$) that can participate in the hydrogen-bonding network, and perylene tetra-carboxylic di-imide includes two functional units ($O=CR-NR-CR=O$) that participate in the hydrogen-bonding network. The three-fold and two-fold symmetry of melamine and perylene tetra-carboxylic di-imide, respectively, results in a hexagonal network, as shown, for example in FIG. 1A. The bimolecular assembly of these molecules defines the pattern of the network (e.g., the hexagonal network shown in FIG. 1A), and results in the formation of pores (e.g., the center of each hexagon shown in FIG. 1A) that are defined by edges of the pattern.

The presence of a plurality of hydrogen bond donors and/or acceptors provides for the formation of the two-dimensional network across the surface of the substrate. As such, while melamine and PTCDI are examples of two molecules that can form the porous molecular network, it is to be understood that other amine and di-imide combinations can be used to form other pattern geometries. As an example, an amine molecule having four of the functional melamine units ($H_2N-C-N-C-NH_2$), and exhibiting a four-fold axis of symmetry, will enable the construction of rectangular, for example, square pores, instead of the hexagonal pores resulting from the use of PTCDI and melamine. This enables the ability to tailor the pore size by the judicious selection of the constituent molecules from which the molecular network is defined.

Examples of suitable amines include melamine:

or analogs thereof. Melamine analogs include at least the functional unit ($H_2N-C-N-C-NH_2$) that participates in the hydrogen-bonding network with the di-imide. An example of a melamine analog includes 4,4',4'-(1,3,5-benzenetriyl)tris-2,6-pyridinediamine:

as well as variants thereof. In an example variant, the central benzene ring is substituted with a different aromatic or other cyclic system that allows a different number (than 3), e.g., 2 or 4, of the 2,6-diaminopyridyl (or other $H_2N-C-N-C-NH_2$-containing) moieties to be attached. In some variants, one or more spacer units, such as alkynylene, bis(alkynylene) or arylene diradicals, may be interposed between the central unit and the pendant 2,6-diaminopyridyl (or other $H_2N-C-N-C-NH_2$-containing) moieties. Another example of a melamine analog includes:

which includes four $H_2N-C-N-C-NH_2$ moieties. While some melamine analogs have been described, it is believed that other aromatic amines or non-aromatic conjugated amines may also be used, as long as the selected amine preferentially undergoes heteromolecular hydrogen bonding with the selected di-imide.

Examples of suitable di-imides include perylene tetra-carboxylic di-imide (PTCDI):

or analogs thereof. PTCDI analogs include at least two di-imide functional units (O=CR—NR—CR=O) that participate in the hydrogen-bonding network with the amine. An example of a PTCDI analog includes:

It is believed that any of the following aromatic moieties may be used as a PTCDI analog after being converted to a di-imide:

I

II

III

IV

V

VI

-continued

VII

VIII

IX

X

-continued

XI

XII

The porous molecular network may be pre-assembled in solution and then deposited on the desired substrate surface. Because the molecules are capable of supramolecular self-assembly, the solution does not include reagents (e.g., a catalyst) other than the solvent and the two constituents of the matrix/network that is to be formed. Examples of the solvent include dimethylsulfoxide (DMSO) and dimethylformamide (DMF). Other solvents may be selected and may depend, in part, upon the two constituents of the matrix/network that is to be formed.

The porous molecular network assembly may be formed in the solution by reaching the thermodynamic equilibrium. One method for reaching the thermodynamic equilibrium is to heat a saturated mixture of perylene tetracarboxylic di-imide or an analog thereof and melamine or an analog thereof. The saturated mixture includes the perylene tetracarboxylic di-imide or an analog thereof and melamine or an analog thereof at a suitable stoichiometry (molar ratio). In an example, the di-imide and amine are present at a mole ratio of 1:1. However, the stoichiometry depends upon the molecules selected and their affinity for the particular substrate surface. If one of the molecules has a higher affinity for the substrate surface, the amount of that molecule in the solution may be lower than the amount of the other molecule in the solution.

The temperature to which the solution is heated depends, in part, upon the two constituents in the solution. In an example, heating takes place at a temperature ranging from about 51° C. (~325 K) to about 127° C. (~400K).

The heated saturated mixture may then be deposited on the substrate (e.g., by any of the methods disclosed herein), and cooled. Cooling may accomplished slowly, e.g., at a rate up to about 10° C. per minute. In an example, the cooling rate ranges from about 0.1° C./minute to about 10° C./minute. In another example, the cooling rate ranges from about 0.5° C./minute to about 5° C./minute. In still another example, the cooling rate is about 1° C./minute.

The porous molecular network that forms on the substrate surface is a non-reactive pi (π) system. In one example, this type of system is essentially chemically inert, and thus will not react with a number or reagents and/or activation methods used to functionalize a substrate surface with surface chemistry; and thus, this type of system readily passivates the substrate surface upon which it is applied. Due in part to this passivation property, the porous molecular network may be used as a pattern to selectively functionalize the substrate surface with surface chemistry. Examples of how the porous molecular network may be used in patterning different flow cells will be described in further detail below.

Moreover, the non-reactive pi (π) system of the porous molecular network means that the porous molecular network is not covalently attached to the underlying substrate surface. As such, the porous molecular network can be readily removed from the substrate surface when desired. For removal of the porous molecular network, a reagent with a higher affinity for the di-imide moiety than the substrate surface itself may be used. This reagent will shift the thermodynamic equilibrium and the porous molecular network will desorb from the substrate surface. Examples of the removal reagent including an oxidizing reagent, which can oxidize the ring of the di-imide moiety. The oxidized di-imide is not planar, and will readily desorb from the substrate surface. A suitable oxidizing reagent is selected from the group consisting of permanganates, perborates, halogens, perchlorates, and peroxides. Examples of when porous molecular network removal may take place will be described in further detail below.

Flow Cell for Optical Detection

In one example disclosed herein, a flow cell includes a substrate; a selectively removable porous molecular network on the substrate and defining exposed substrate regions; and sequencing surface chemistry on at least some of the exposed regions, wherein the surface chemistry includes an activated layer, a polymer layer attached to the activated layer, and a primer attached to the polymer layer.

Figure 1A:
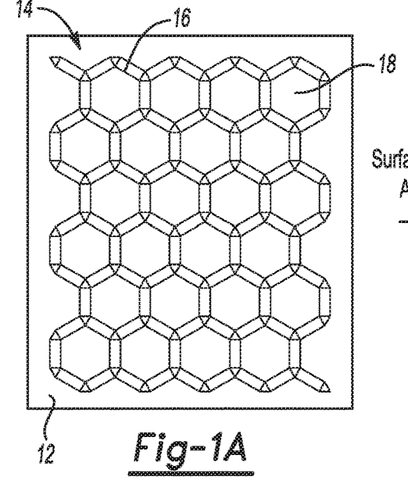
FIGS. 1A and 1B are top, schematic views depicting an example of a method of forming an example of a flow cell disclosed herein.
Figure 1B:
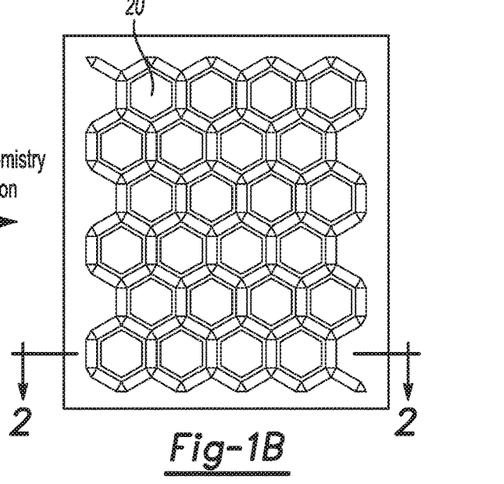
Figure 2:
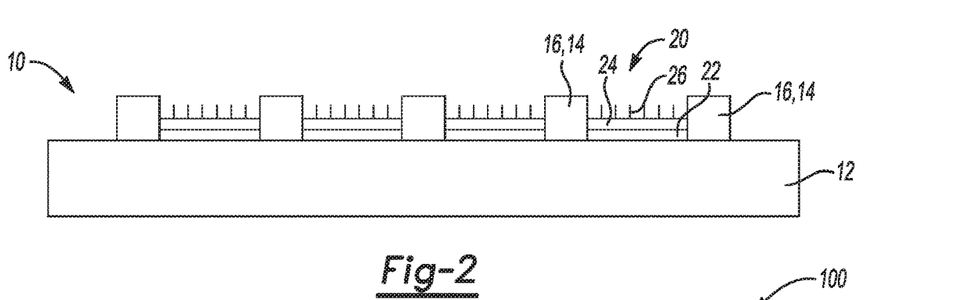
FIG. 2 is a cross-sectional view of the flow cell taken along line 2-2 of FIG. 1B.

An example of a method for making this flow cell is shown schematically in FIG. 1A and FIG. 1B. The method includes applying a porous molecular network 14 to a substrate 12 to define a pattern of exposed substrate regions 18 (FIG. 1A); and applying surface chemistry 20 to at least some of the exposed substrate regions 18 (FIG. 1B). As shown in FIG. 2, in this example method, the application of the surface chemistry 20 includes activating the exposed substrate regions 18 to form activated pads 22; applying a respective polymer layer 24 to each of the activated pads; and grafting a primer 26 to each of the respective polymer layers 24.

FIG. 1A illustrates a top schematic view of the substrate 12 having the porous molecular network 14 self-assembled thereon.

Examples of suitable substrates 12 include epoxy siloxane, glass and modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($TaO_5$) or other tantalum oxide(s) ($TaO_x$), hafnium oxide ($HaO_2$), carbon, metals, inorganic glasses, or the like. The support may also be glass or silicon, with a coating layer of tantalum oxide or another ceramic oxide at the surface.

In an example, the substrate 12 may have a diameter ranging from about 2 mm to about 300 mm, or a rectangular sheet or panel having its largest dimension up to about 10 feet (~3 meters). In an example, the substrate is a wafer having a diameter ranging from about 200 mm to about 300 mm. In another example, the support is a die having a width ranging from about 0.1 mm to about 10 mm. While example dimensions have been provided, it is to be understood that a support with any suitable dimensions may be used. For another example, a panel may be used that is a rectangular support, which has a greater surface area than a 300 mm round wafer.

The porous molecular network 14 includes a pattern 16, which is defined by the self-assembled amine and di-imide molecules, and pores, which are defined by the pattern 16. The pattern 16 cover portions of the substrate 12, and the pores correspond to the exposed substrate regions 18. The porous molecular network 14 may be pre-assembled and deposited on the substrate 12 as described herein. Rinsing and drying may be performed prior to applying the surface chemistry 20.

As mentioned above, the application of the surface chemistry 20 in this example method initially involves activating the exposed substrate regions 18. In some examples, activation involves silanizing the exposed substrate regions with a silane or silane derivative. The silane or silane derivative used in silanizing has no affinity for the extended pi system of the porous molecular network 14, and thus the porous molecular network 14 effectively defines isolated anchor points (e.g., the exposed substrate regions 18) on the substrate 12 where the silane or silane derivative will react.

When the exposed substrate regions 18 are activated via silanization, silanization may be accomplished using any silane or silane derivative. The selection of the silane or silane derivative may depend, in part, upon the polymer layer 24 that is to be formed, as it may be desirable to form a covalent bond between the silane or silane derivative and the polymer layer 24. The method used to attach the silane or silane derivative to the exposed substrate regions 18 may vary depending upon the silane or silane derivative that is being used. Several examples are set forth herein.

Examples of suitable silanization methods include vapor deposition (e.g., a YES method), spin coating, or other deposition methods.

In an example utilizing the YES CVD oven, the substrate 12 having the porous molecular network 14 thereon is placed in the CVD oven. The chamber may be vented and then the silanization cycle started. During cycling, the silane or silane derivative vessel may be maintained at a suitable temperature (e.g., about 120° C. for norbornene silane), the silane or silane derivative vapor lines be maintained at a suitable temperature (e.g., about 125° C. for norbornene silane), and the vacuum lines be maintained at a suitable temperature (e.g., about 145° C.).

In another example, the silane or silane derivative (e.g., liquid norbornene silane) may be deposited inside a glass vial and placed inside a glass vacuum desiccator with the substrate 12 having the porous molecular network 14 thereon. The desiccator can then be evacuated to a pressure ranging from about 15 mTorr to about 30 mTorr, and placed inside an oven at a temperature ranging from about 60° C. to about 125° C. Silanization is allowed to proceed, and then the desiccator is removed from the oven, cooled and vented in air.

Vapor deposition, the YES method and/or the vacuum desiccator may be used with a variety of silane or silane derivatives, such as those silane or silane derivative including a cycloalkene unsaturated moiety, such as norbornene, a norbornene derivative (e.g., a (hetero)norbornene including an oxygen or nitrogen in place of one of the carbon atoms), transcyclooctene, transcyclooctene derivatives, transcyclopentene, transcycloheptene, trans-cyclononene, bicyclo[3.3.1]non-1-ene, bicyclo[4.3.1]dec-1 (9)-ene, bicyclo[4.2.1]non-1(8)-ene, and bicyclo[4.2.1]non-1-ene. Any of these cycloalkenes can be substituted, for example, with an R group, such as hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An example of the norbornene derivative includes [(5-bicyclo[2.2.1]hept-2-enyl)ethyl]trimethoxysilane. As other examples, these methods may be used when the silane or silane derivative includes a cycloalkyne unsaturated moiety, such as cyclooctyne, a cyclooctyne derivative, or bicyclononynes (e.g., bicyclo[6.1.0]non-4-yne or derivatives thereof, bicyclo[6.1.0]non-2-yne, or bicyclo[6.1.0]non-3-yne). These cycloalkynes can be substituted with any of the R groups described herein.

The attachment of the silane or silane derivative forms activated pads 22 on at least some of the exposed substrate regions 18. Because the silane or silane derivative reacts with the substrate 12 and does not react with the pattern 16, respective activated pads 22 are formed on the exposed substrate regions 18. In this example, the activated pads 22 are isolated from one another by the pattern 16.

The polymer layer 24 may then be applied to the activated pads 22. The polymer layer 24 may be a semi-rigid polymeric material that is permeable to liquids and gases. The molecule used to form the polymer layer 24 may be selected to preferentially react with the activated pads 22 rather than the porous molecular network 14. In some instances, the molecule may be very reactive toward the activated pads 22 and have very little or no affinity for porous molecular network. This enhances the specificity of the molecule reactivity, and enables the molecule to form respective polymer layers 24 on the activated pads 22 and not on the porous molecular network 14.

An example of the polymer layer 24 includes an acrylamide copolymer, such as poly(N-(5-azidoacetamidylpentyl)acrylamide-co-acrylamide, PAZAM. PAZAM and some other forms of the acrylamide copolymer are represented by the following structure (I):

wherein:
$R^1$ is H or optionally substituted alkyl;
$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
$R^5$, $R^6$, and $R^8$ are each independently selected from the group consisting of H and optionally substituted alkyl;
each of the —$(CH_2)_p$— can be optionally substituted;
p is an integer in the range of 1 to 50;
n is an integer in the range of 1 to 50,000; and
m is an integer in the range of 1 to 100,000.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of the PAZAM may range from about 10 kDa to about 1500 kDa, or may be, in a specific example, about 312 kDa.

In some examples, PAZAM is a linear polymer. In some other examples, PAZAM is a lightly cross-linked polymer.

In other examples, the polymer layer 24 may be a variation of the structure (I). In one example, the acrylamide unit may be replaced with N,N-dimethylacrylamide In this example, the acrylamide unit in structure (I) may be replaced with where $R_6$, $R_7$, and $R_8$ are each H, and $R_9$ and $R_{10}$ are each a methyl group (instead of H as is the case with the acrylamide). In this example, q may be an integer in the range of 1 to 100,000. In another example, the N,N-dimethylacrylamide may be used in addition to the acrylamide unit. In this example, structure (I) may include in addition to the recurring "n" and "m" features, where $R_6$, $R_7$, and $R_8$ are each H, and $R_9$ and $R_{10}$ are each a methyl group. In this example, q may be an integer in the range of 1 to 100,000.

It is to be understood that other molecules may be used to form the polymer layer 24, as long as they are functionalized to interact with the activated pads 22 and the subsequently applied primer(s) 26. Other examples of suitable molecules for forming the polymer layer 24 include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable molecules for forming the polymer layer 24 include mixed copolymers of acrylamides and acrylates.

As mentioned herein, the molecule used to form the polymer layer 24 has no (or very little) affinity for the extended pi system of the porous molecular network 14, and thus polymer layer 24 will form on the activated pad 22 rather than on the porous molecular network 14. The molecule (e.g., PAZAM) may be deposited using spin coating, or dipping or dip coating, or flow of the functionalized molecule under positive or negative pressure, or another suitable technique. The functionalized molecule may be present in a mixture. In an example, the mixture includes PAZAM in water or in an ethanol and water mixture. The molecule will react to form the polymer layer 24 on the activated pads 22 and not on the porous molecular network 14.

After being coated, the molecule may also be exposed to a curing process to form the polymer layer 24 across each of the activated pads 22. In an example, curing the functionalized molecule may take place at a temperature ranging from room temperature (e.g., about 25° C.) to about 95° C. for a time ranging from about 1 millisecond to about several days. In another example, the time may range from 10 seconds to at least 24 hours. In still another example, the time may range from about 5 minutes to about 2 hours.

The attachment of the polymer layer 24 to the activated pads 22 may be through covalent bonding. The covalent linking of the polymer layer 24 to the activated pads 22 is helpful for maintaining the surface chemistry 20 at the respective isolated areas throughout the lifetime of the ultimately formed flow cell during a variety of uses. The following are some examples of reactions that can take place between the activated pads 22 and the polymer layer 24.

When the silane or silane derivative includes norbornene or a norbornene derivative as the unsaturated moiety, the norbornene or a norbornene derivative can: i) undergo a 1,3-dipolar cycloaddition reaction with an azide/azido group of PAZAM; ii) undergo a coupling reaction with a tetrazine group attached to PAZAM; undergo a cycloaddition reaction with a hydrazone group attached to PAZAM; undergo a photo-click reaction with a tetrazole group attached to PAZAM; or undergo a cycloaddition with a nitrile oxide group attached to PAZAM.

When the silane or silane derivative includes cyclooctyne or a cyclooctyne derivative as the unsaturated moiety, the cyclooctyne or cyclooctyne derivative can: i) undergo a strain-promoted azide-alkyne 1,3-cycloaddition (SPAAC) reaction with an azide/azido of PAZAM, or ii) undergo a strain-promoted alkyne-nitrile oxide cycloaddition reaction with a nitrile oxide group attached to PAZAM.

When the silane or silane derivative includes a bicyclononyne as the unsaturated moiety, the bicyclononyne can undergo similar SPAAC alkyne cycloaddition with azides or nitrile oxides attached to PAZAM due to the strain in the bicyclic ring system.

A grafting process is performed in order to graft a primer 26 to the polymer layers 24. The primer 26 may be any forward amplification primer or reverse amplification primer that includes an alkyne functional group, or another terminated primer. Other examples of terminated primers that may be used include a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, and a triazolinedione terminated primer. A mixture of primers may also be used. Specific examples of suitable primers include P5 and/or P7 primers, which are used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, ISEQ™, GENOME ANALYZER™, etc., and other instrument platforms.

In an example, grafting may be accomplished by flow through deposition (e.g., using a temporarily bound lid), dunk coating, spray coating, puddle dispensing, or by another suitable method that will attach the primer(s) 26 to the polymer layers 24. Each of these example techniques may utilize a primer solution or mixture, which may include the primer(s), water, a buffer, and a catalyst.

Dunk coating may involve submerging the substrate 12 (with the activated pads 22 and polymer layers 24 thereon) into a series of temperature controlled baths. The baths may also be flow controlled and/or covered with a nitrogen blanket. The baths may include the primer solution or mixture. Throughout the various baths, the primer(s) 26 will attach to functional group(s) of the polymer layers 24. In an example, the substrate 12 will be introduced into a first bath including the primer solution or mixture where a reaction takes place to attach the primer(s) 26, and then moved to additional baths for washing. Movement from bath to bath may involve a robotic arm or may be performed manually. A drying system may also be used in dunk coating.

Spray coating may be accomplished by spraying the primer solution or mixture directly onto the substrate 12 (with the activated pads 22 and polymer layers 24 thereon). The spray coated wafer may be incubated for a time ranging from about 4 minutes to about 60 minutes at a temperature ranging from about 0° C. to about 70° C. After incubation, the primer solution or mixture may be diluted and removed using, for example, a spin coater.

Puddle dispensing may be performed according to a pool and spin off method, and thus may be accomplished with a spin coater. The primer solution or mixture may be applied (manually or via an automated process) to the substrate 12 (with the activated pads 22 and polymer layers 24 thereon). The applied primer solution or mixture may be applied to or spread across the entire surface, including on the pattern 16. The primer coated substrate 12 may be incubated for a time ranging from about 2 minutes to about 60 minutes at a temperature ranging from about 0° C. to about 80° C. After incubation, the primer solution or mixture may be diluted and removed using, for example, the spin coater.

The primers 26 react with functional groups of the polymer layers 24 and have no affinity for the extended pi system of the porous molecular network 14. As such, the primers 26 graft to the polymer layer 24 rather than on the porous molecular network 14.

In another example of the method, application of the surface chemistry 20 may take place before and after the application of the porous molecular network. In these other examples, substrate surface activation takes place prior to the application of the porous molecular network 14, and polymer layer 24 formation and primer 26 grating take place after the application of the porous molecular network.

In this example, the surface of the (bare) substrate 12 is exposed to plasma ashing, which generates surface-activating agent(s) (e.g., —OH groups) on the surface of the substrate 12. It is noted that the addition of —OH groups can reduce the affinity of the substrate 12 to the porous molecular network (which is hydrophobic), and thus the conditions and timing of plasma ashing may be controlled so that the surface is not too hydrophilic.

In this example, the porous molecular network 14 is added on the activated substrate surface, which exposes discrete regions of the activated substrate surface. When the porous molecular network 14 is applied over the activated substrate, the activated pads 22 are formed.

Also in this example, the polymer layer 24 may then be selectively applied to the activated pads 22 as described herein, and primers 26 may be grafted to the polymer layer 24 as described herein.

Referring now to FIG. 2, an example of the flow cell 10 formed by the method shown in FIG. 1A and FIG. 1B (e.g., patterning and then addition of the surface chemistry 20) is depicted. While a single type of primer 24 is shown, it is to be understood that two or more different primers 24 may be attached.

In this example, the X and Y dimensions of each discrete section of the surface chemistry 20 substantially correspond with the X and Y dimensions of each pore of the porous molecular network 14. The pores of the porous molecular network 14 enable ordering of the surface chemistry 20 at nanometer precision.

In the example shown in FIG. 2, the selectively removable porous molecular network 14 remains on the substrate 12 throughout the described method, and then as part of the flow cell 10 during a subsequent sequencing operation. This may be desirable when the molecular structure of the porous molecular network 14 will not interact with fluorophores that are to be used during the sequencing operation. In this example, the scaffold of the molecular network 14 can help passivate the surface toward non-specific absorption of biomolecules during the sequencing operation.

Figure 3A:
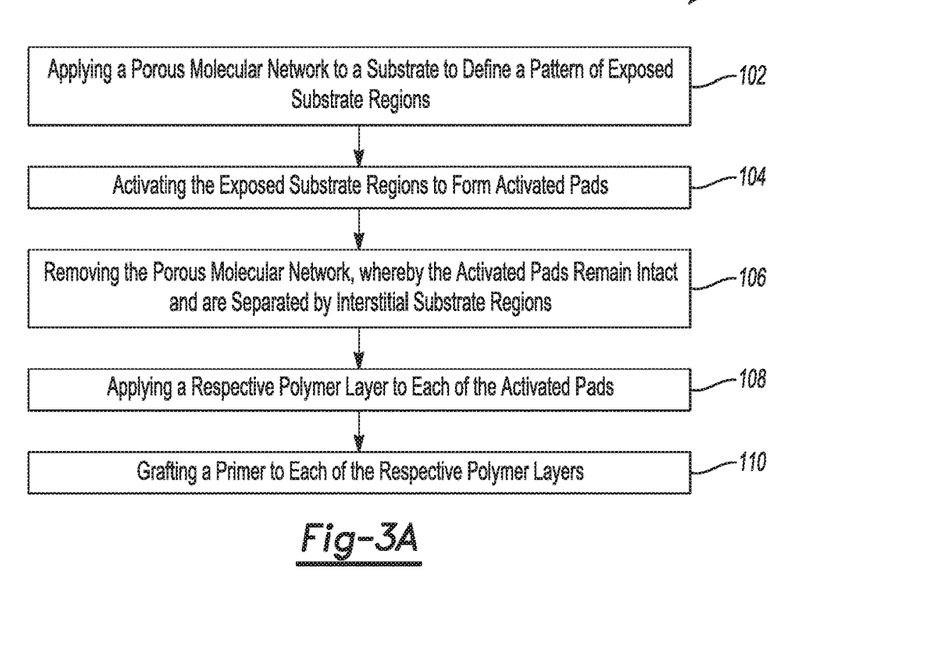
FIG. 3A is a flow diagram illustrating another example of a method disclosed herein.
Figure 3B:
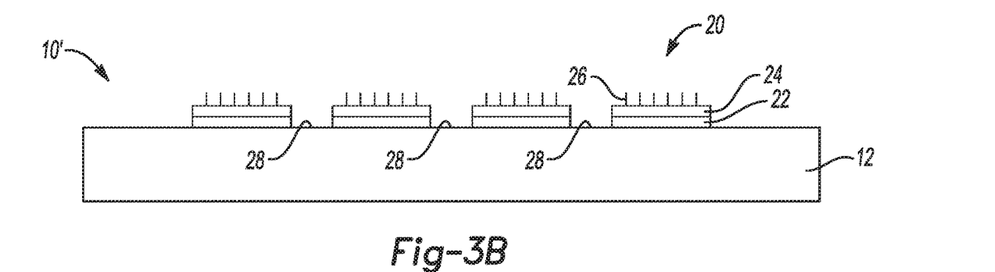
FIG. 3B is a cross-sectional view of an example of flow cell formed by the method shown in FIG. 3A.

In other examples, the selectively removable porous molecular network 14 may be removed from the substrate 12 during the method, and then is not present as part of the flow cell during a subsequent sequencing operation. An example of this method 100 is shown in FIG. 3A and an example of the resulting flow cell 10' is shown in FIG. 3B. This method 100 includes applying a porous molecular network 14 to a substrate 12 to define a pattern of exposed substrate regions 18 (reference numeral 102); activating the exposed substrate regions 18 to form activated pads 22 (reference numeral 104); removing the porous molecular network 14, whereby the activated pads 22 remain intact and are separated by interstitial substrate regions 28 (reference numeral 104); applying a respective polymer layer 24 to each of the activated pads 22 (reference numeral 106); and grafting a primer 26 to each of the respective polymer layers 24 (reference numeral 108). This method 100 may be desirable when the molecular structure of the porous molecular network 14 is capable of interacting with fluorophores that are to be used during the sequencing operation. Some fluorophores may stick to some examples of the porous molecular network 14. This interaction would disrupt or otherwise deleteriously affect sequencing because fluorophore-labeled analytes that are stuck to the porous molecular network 14 cannot interact with a sequencing template. In these examples, the method 100 may be used, which effectively utilizes the porous molecular network 14 to create the activated pads 22 (anchor points for the remaining of the surface chemistry 20), and then removes the porous molecular network 14 so that it does not interfere with a subsequent sequencing operation. In these examples, the fingerprint and potential interference of the porous molecular network 14 is removed.

In the method 100, the porous molecular network 14 may be formed as described herein, and activation may occur as described herein using the silane or silane derivative. In this example, the X and Y dimensions of each discrete activated pad 22 (and thus each section of the surface chemistry 20) correspond with the X and Y dimensions of each pore of the porous molecular network 14 as the silane or silane derivative activates the exposed substrate regions 18 at the pores.

After the activated pads 22 are formed, the method 100 then includes removing the porous molecular network 14. The chemical nature of the porous molecular network 14 renders it susceptible to any of the oxidizing reagents disclosed herein. The oxidizing reagent may be deposited on the porous molecular network 14 (and on the remainder of the substrate 12) using any suitable deposition technique. Exposure to the oxidizing reagent lifts the porous molecular network 14 from the substrate 12 (e.g., via desorption), due to the oxidation of the di-imide. The oxidizing reagent does not react with the activated pads 22, and thus these activated portions of the substrate 12 remain intact for subsequent reaction. The substrate 12 and activated pads 22 thereon may be washed (e.g., with water) after the porous molecular network 14 is removed.

The removal of the porous molecular network 14 exposes portions of the substrate 12, which are referred to herein as interstitial regions 28. The interstitial regions 18 may be continuous (and have the same pattern as the porous molecular network 14), whereas the silanized regions 22 are discrete.

In the method 100, the polymer layers 24 may be formed as described herein. In these examples, the molecule used to form the polymer layer 24 has no affinity for the substrate 12, and thus polymer layer(s) 24 will selectively form on the silanized pad(s) 22 rather than on the interstitial regions 28 of the substrate 12. In the method 100, primer grafting 26 may also occur as described herein.

The flow cells 10, 10' disclosed herein may be used in a variety of sequencing approaches or technologies, including techniques often referred to as sequencing-by-synthesis (SBS), cyclic-array sequencing, sequencing-by-ligation, pyrosequencing, and so forth. With any of these techniques, since the primer(s) 26 are present as part of the surface chemistry 20 not on the pattern 16 or interstitial regions 28, sequencing will be confined to the surface chemistry 20.

As one example, a sequencing by synthesis (SBS) reaction may be run on a system such as the HISEQ™, HISEQX™, MISEQ™, MISEQDX™, MINISEQ™, NOVASEQ™, NEXTSEQDX™, or NEXTSEQ™, or any other sequencer systems from Illumina, Inc. (San Diego, Calif.). In SBS, extension of a sequencing primer along a nucleic acid template (i.e., the sequencing template) is monitored to determine the sequence of nucleotides in the template. The underlying chemical process can be polymerization (e.g., catalyzed by a polymerase enzyme) or ligation (e.g., catalyzed by a ligase enzyme).

In a particular polymerase-based SBS process, a nucleic acid library template is introduced to the flow cell 10, 10', whereby the nucleic acid library template hybridizes to a primer 26. Multiple nucleic acid library templates are hybridized, for example, to one of two types of primers 26 immobilized on the flow cell 10, 10'. Cluster generation may then be performed. In one example of cluster generation, the nucleic acid library templates are copied from the hybridized primers 26 by 3' extension using a high-fidelity DNA polymerase. The original nucleic acid library templates are denatured, leaving the copies immobilized where primers 26 are located. Isothermal bridge amplification may be used to amplify the immobilized copies. For example, the copied templates loop over to hybridize to an adjacent, complementary primer 26, and a polymerase copies the copied templates to form double stranded bridges, which are denatured to form two single stranded strands. These two strands loop over and hybridize to adjacent, complementary primers 26 and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template strands.

The 3' end of the templates and any primers 26 can be blocked to prevent unwanted priming. A sequencing primer can be introduced to the flow cell 10, 10'. Because the sequencing primer is complementary to an adapter of the nucleic acid template strand, it will hybridize to the adapter (e.g., a read 1 sequencing primer of the template).

Fluorescently labeled nucleotides are added to the template (thereby extending the sequencing primer) in a template dependent fashion such that detection of the order and type of nucleotides added to the primer can be used to determine the sequence of the template. For example, to initiate a first SBS cycle, one or more labeled nucleotides, DNA polymerase, etc., may be delivered into/through the flow channel, etc. that houses an array of primers 26 having template strands attached thereto. Sequencing primer extension causes a labeled nucleotide to be incorporated, and this incorporation can be detected through an imaging event. During an imaging event, an illumination system (not shown) may provide an excitation light to the surface chemistry 20.

In some examples, the nucleotides can further include a reversible termination property that terminates further primer extension once a nucleotide has been added. For example, a nucleotide analog having a reversible terminator moiety can be added to the sequencing primer along the template strand such that subsequent extension cannot occur until a deblocking agent is delivered to remove the moiety. Thus, for examples that use reversible termination, a deblocking reagent can be delivered to the flow channel, etc. (before or after detection occurs).

Wash(es) may take place between the various fluid delivery steps. The SBS cycle can then be repeated n times to extend the sequencing primer by n nucleotides, thereby detecting a sequence of length n.

While SBS has been described in detail, it is to be understood that the flow cells 10, 10' described herein may be utilized with other sequencing protocol, for genotyping, or in other chemical and/or biological applications. In yet another example, the flow cells 10, 10' disclosed herein may be used for on-cell library generation.

Flow Cell for Electrical Detection

In another example disclosed herein, a flow cell includes a substrate; a selectively removable porous molecular network on the substrate and defining exposed substrate regions; and sequencing surface chemistry on at least some of the exposed regions, wherein the surface chemistry includes a nanostructure and an enzyme attached to the nanostructure.

Figure 4:
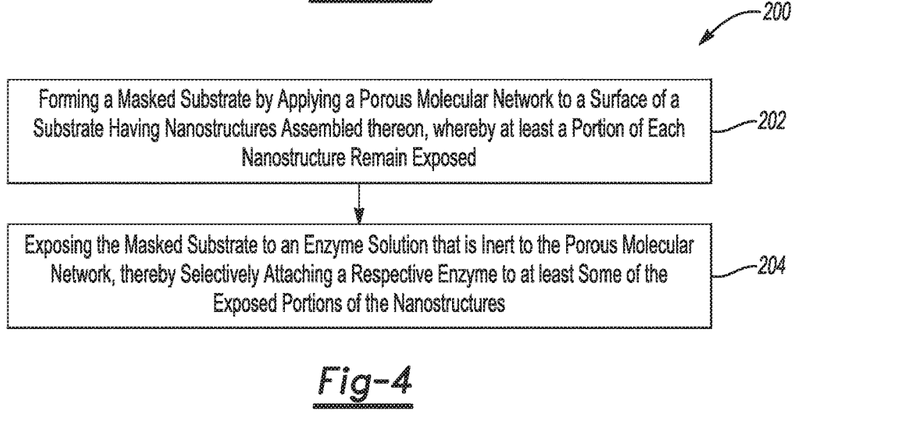
FIG. 4 is a flow diagram illustrating another example of a method disclosed herein.
Figure 5A:
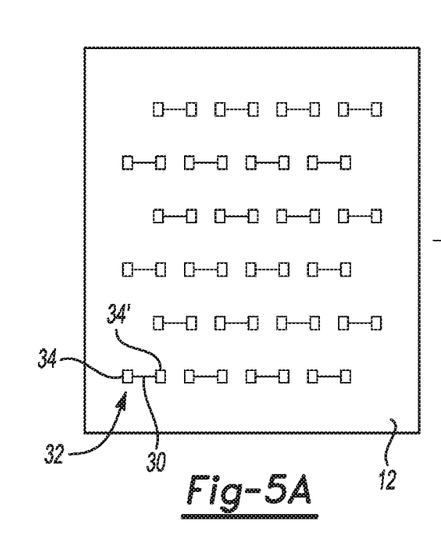
FIGS. 5A through 5C are top, schematic views depicting an example of the method of FIG. 4.
Figure 5B:
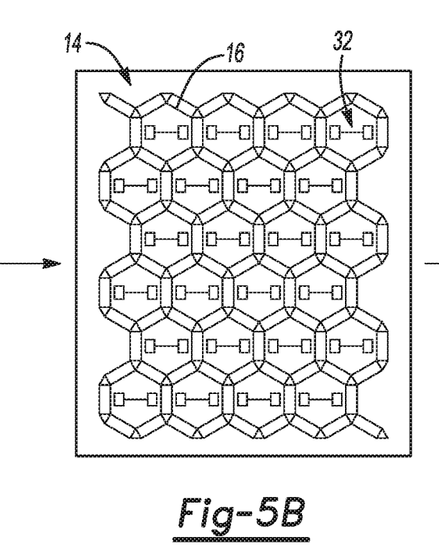
Figure 5C:
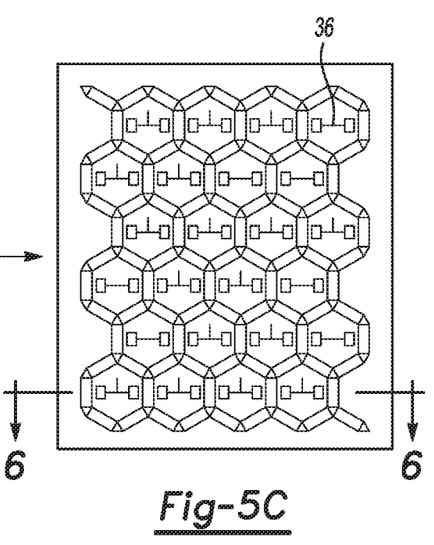

An example of a method for making this flow cell is shown in FIG. 4 and in FIG. 5A through FIG. 5C.

As shown in FIG. 4, the method 200 includes forming a masked substrate by applying a porous molecular network 14 to a surface of a substrate 12 having nanostructures assembled thereon, whereby at least a portion of each nanostructure remain exposed (reference numeral 202); and exposing the masked substrate to an enzyme solution that is inert to the porous molecular network 14, thereby selectively attaching a respective enzyme to at least some of the exposed portions of the nanostructures (reference numeral 204).

FIG. 5A illustrates a top schematic view of the substrate 12 having the nanostructures assembled thereon. The substrate 12 may be any of the examples described herein.

The nanostructure is shown at reference numeral 30 in FIG. 5A. The nanostructure 30 is a conductive channel of a charge sensor 32, which also includes electrodes 34, 34'. As used herein, the term "charge sensor" is intended to mean a detection device that translates perturbations at its surface or in its surrounding electrical field into an electrical signal. For example, a charge sensor 32 can translate the arrival or departure of a reaction component into an electrical signal. In some examples, the charge sensor 32 can also translate interactions between two reaction components (e.g., a template nucleic acid and a nucleotide) into an electrical signal. An example charge sensor 32 is a field effect transistor (FET), such as a carbon nanotube (CNT) based FET, single-walled carbon nanotube (SWNT) based FET, silicon nanowire (SiNW) FET, a polymer nanowire FET, and a graphene nanoribbon FET (and related nanoribbon FETs fabricated from 2D materials such as $MoS_2$, silicene, etc). In a field effect transistor, current flows along a conducting path (the conductive channel/nanostructure 30) that is connected to two electrodes 34, 34' (the source and the drain). The channel conductance between the source and the drain is switched on and off by a third (gate) electrode that can be capacitively coupled through a thin dielectric layer.

Any type of nanostructure 30 can be used, as long as it can function as the conductive channel for the charge sensor 32. Example materials suitable for conductive channels include conductors (e.g., metals, carbon-based materials, some metal oxides, conductive polymers, etc.) or semiconductors (e.g., silicon, other metal oxides, etc.). The nanostructure 30 may have any suitable geometry, such as a tube, wire, ribbon, etc., and at least one dimension (e.g., length, width, diameter, etc.) of the nanostructure 30 may be on the nanoscale. As examples, the nanostructure 30 is a conductive channel including a material selected from the group consisting of a conductor and a semiconductor, and having a geometry selected from the group consisting of a tube, a wire, and a ribbon. Some specific examples of the nanostructure 30 include a carbon nanotube (CNT), a single walled carbon nanotube (SWCN), a silicon nanowire (SiNW), a polymer nanowire, a nanoribbon (e.g., a graphene nanoribbon, a nanoribbon fabricated from 2D materials such as $MoS_2$, silicene, etc.), or any other nanostructure that can function as a conductive channel of the charge sensor 32. In an example, the nanostructure 30 is a silicon nanowire. In another example, the nanostructure is a carbon nanotube.

As shown in FIG. 5A, opposed ends of the nanostructure 30 are in electrical communication with the respective electrodes 34, 34'. Any suitable electrode material may be used that can chemically and electrically attach to the nanostructure 30. Examples of suitable electrode materials include gold, platinum, carbon, indium tin oxide, etc.

In some examples, assembling the charge sensor(s) 32 on the substrate 12 may include fabricating the electrodes 34, 34' and fabricating the nanostructure 30 between the electrodes 34, 34' using any suitable technique, such as direct growth, solution dropping, or various printing techniques. As one example, a carbon nanotube may be produced using arc discharge, laser ablation, high-pressure carbon monoxide disproportionation, or chemical vapor deposition (CVD). As another example, silicon nanowires (SiNWs) may be produced from a silicone precursor by etching of a solid or through catalyzed growth from a vapor or liquid phase.

Each charge sensor 32 may be individually wired (and thus individually monitored). In other words, the electrodes 34, 34' of any individual charge sensor 32 may be connected to electronic circuitry that enables their operation (e.g., once hooked up to a detector and power supply). The electronic circuitry may be electrically connectable to the detector and to the power supply.

The arrangement of the charge sensors 32 on the substrate 12 may be based, in part, on the geometry of the pattern 16, and in particular of the pores, of the porous molecular network 14 that is to be formed on the substrate 12. This is due, in part, to the fact that the porous molecular network 14 will self-assemble on the substrate 12 and on the charge sensors 32, and that it is desirable for at least a portion of the nanostructure 30 to be located in the pores of the porous molecular network 14. The porous molecular network 14 may be partially deposited on the top of the surface of the nanostructure 30 to limit the amount of functionalization taking place on the nanostructure 30 and/or to space out biomolecules attached to the nanostructures 30 and/or to passivate portions of charge sensor 32 to prevent reagents (e.g., solution salts, etc.) from interacting with the passivated portions.

As shown at reference numeral 202 of FIG. 4, the method 200 includes forming a masked substrate by applying a porous molecular network 14 to a surface of a substrate 12 having nanostructures 30 assembled thereon, whereby at least a portion of each nanostructure 30 remain exposed. The porous molecular network 14 may be pre-assembled in solution and then deposited on the substrate 12 as described herein.

Figure 6:
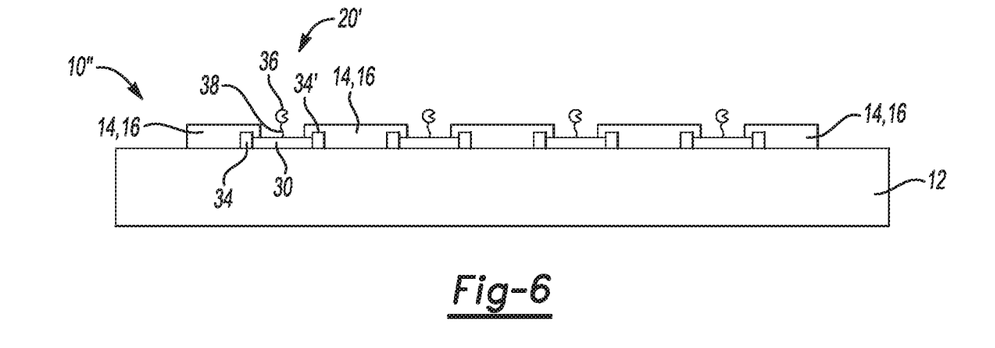
FIG. 6 is a cross-sectional view taken along line 6-6 of FIG. 5C, except that the porous molecular network shown in FIG. 6 is a different example than that which is shown in FIG. 5C.

The porous molecular network 14 will self-assemble on the surface of the substrate 12, and, in some instances, on the components (30, 34, 34') of the charge sensor 32 depending, at least in part, on the size of the pores and the size and location of the charge sensor 32. When deposited, the porous molecular network will self-assemble so that portions of the substrate 12 and/or portions of the charge sensors 32 on the substrate 12 will be exposed at the pores. This forms the masked substrate, as shown in FIG. 5B. To simply and clearly illustrate the porous molecular network 14 and the charge sensors 32, each charge sensor 32 in FIG. 5B is shown as being exposed at a respective pore of the porous molecular network 14. However, it is to be understood that the individual pores of the porous molecular network 14 are smaller than the charge sensor 32, and, in some instances, are smaller than the nanostructure 30. As such, the porous molecular network 14 may cover the electrodes 34, 34' and/or some or all of the nanostructure 30 of the charge sensors 32, in addition to the exposed substrate 12. An example of the porous molecular network 14 extending over the electrodes 34, 34' and some of the nanostructure 30 is shown in FIG. 6. It is to be understood that what is covered by the porous molecular network 14 and what is exposed at the pores of the porous molecular network 14 will depend, in part, upon the dimensions and positioning of the charge sensors 32 and the self-assembly of the porous molecular network 14. In the examples disclosed herein, at least some of the pores of the porous molecular network 14 will expose portions of at least some of the nanostructures 30, although it is to be understood that some nanostructures 30 may be completely covered by the porous molecular network 14 and/or that portions of the substrate 12 may also be exposed at some of the pores.

The method 200 then includes exposing the masked substrate to an enzyme solution that is inert to the porous molecular network 14. By "inert," it is meant that the enzyme solution will not stick to or react with the porous molecular network, and thus the enzymes in the solution will selectively attach to at least some of the exposed portions of the nanostructures 30. The inertness of the enzyme solution may be due to the hydrophilicity of the solution and the hydrophobicity of the porous molecular network 14. The porous molecular network 14 is conjugated and thus is very hydrophobic. The enzyme solution is hydrophilic (compared to the porous molecular network 14), and thus will not stick to or react with the porous molecular network 14. As such, when the masked substrate is exposed to the enzyme solution, the enzymes in solution may be attracted to any of the exposed portions of the nanostructures 30 rather than to the porous molecular network 14. Since the porous molecular network 14 may cover some of the surface of some or all of the nanostructures 30, only small portions of these nanostructure(s) 30 may be exposed at the pores. The small exposed portion limits the functionalization that can occur at any one nanostructure 30, which can improve the specificity of biomolecule attachment. In some examples, the small exposed nanostructure portion can attach a single enzyme, which can improve the sensing function of the charge sensor 32.

The enzyme solution may include the enzyme 36 (alone or in combination with a tether 38 which is attached thereto) and a liquid carrier of the enzyme. The liquid carrier will be a water-based solution. In one example, a saline solution may be used as the liquid carrier.

In the examples disclosed herein, it is desirable for a single enzyme 36 to attach to a single nanostructure 30 (as shown in FIG. 5C and FIG. 6). To aid in this process, the enzyme 36 used may be selected to have a hydrodynamic radius in solution that is similar to the size of the portion of the nanostructure 30 that may be exposed at the pores of the pattern 16. By "similar," it is meant that the hydrodynamic radius may be up to 50% larger or smaller than the size of the pore of the porous molecular network. An example of a suitable enzyme 36 is a polymerase. Examples of suitable DNA polymerases include those classified by structural homology into families identified as A, B, C, D, X, Y, and RT. DNA Polymerases in Family A include, for example, T7 DNA polymerase, eukaryotic mitochondrial DNA Polymerase γ, *E. coli* DNA Pol I, *Thermus aquaticus* Pol I, and *Bacillus stearothermophilus* Pol I. DNA Polymerases in Family B include, for example, eukaryotic DNA polymerases α, δ, and ε; DNA polymerase ζ; T4 DNA polymerase, Phi29 DNA polymerase, and RB69 bacteriophage DNA polymerase. Examples in Family C include, for example, the *E. coli* DNA Polymerase III alpha subunit. Examples in Family D include, for example, polymerases derived from the Euryarchaeota subdomain of Archaea. DNA Polymerases in Family X include, for example, eukaryotic polymerases Pol β, Pol σ, Pol λ, and Pol μ, and *S. cerevisiae* Pol4. DNA Polymerases in Family Y include, for example, Pol η, Pol iota, Pol kappa, *E. coli* Pol IV (DINB) and *E. coli* Pol V (UmuD'2C). The RT (reverse transcriptase) family of DNA polymerases includes, for example, retrovirus reverse transcriptases and eukaryotic telomerases.

The enzyme 36 may be directly attached to the exposed portion of the nanostructure 30 or indirectly attached to the exposed portion of the nanostructure 30, e.g., through a tether 38 (shown in FIG. 6). The attachment between the enzyme 36 and the exposed portion of the nanostructure 30, or between the enzyme 36 and the tether 38 and between the tether 38 and the exposed portion of the nanostructure 30 may be covalent or non-covalent, and may depend upon the material of the nanostructure 30, the enzyme 36, and any tether 38 that is used. In an example, the attachment is accomplished using nickel NTA/His tag chemistry.

The tether 38 may be used as an anchor for the enzyme 36 (e.g., polymerase). Examples of a suitable tether 38 include polyethylene glycol (PEG), a DNA chain, a peptide nucleic acid (PNA) chain, an aliphatic hydrocarbon chain, etc. In some examples, the tether 38 length is sufficient to hold the enzyme 36 at least 10 nm away from the nanostructure 30. This may be desirable, for example, so that conformal changes to the polymerase (or other enzyme 36), charges of the polymerase (or other enzyme 36), and/or charges of the target/template polynucleotide chain held by the polymerase (or other enzyme 36) do not interfere with the sensing operation of the nanostructure 30.

When the masked substrate is exposed to the enzyme solution, heating may be performed in order to couple the enzyme 36 or tether 38 to the exposed portion(s) of any nanostructure(s) 30. It is to be understood, however, that some coupling reactions (e.g., amide coupling) may take place at room temperature (e.g., ranging from about 18° C. to about 25° C.), and thus the use of additional heating may depend upon the enzyme 36 or tether 38, the nanostructure 30, and the type of coupling reaction that is taking place between the components 36 and 30 or 38 and 30.

An example of the flow cell 10" shown in FIG. 6 is formed as a result of the method 200. While each of the nanostructures 30 in an array maybe functionalized with an enzyme 36, it is to be understood that, in some examples, the coupling reaction may not take place at all of the nanostructures 30 and thus some (but not all) of the nanostructures 30 in an array maybe functionalized with an enzyme 36. In this example flow cell 10", the porous molecular network 14 may remain on the substrate 12 and on the covered portions of the charge sensor 32 during a subsequent sequencing operation. Since the detection is electronic and does not involve fluorophores, the hydrophobic porous molecular network 14 can help to guide introduced reagents (which are hydrophilic) to the enzyme-functionalized nanostructure 30.

While not shown in FIG. 6, it is to be understood that each charge sensor 32 may also include a detector that can detect an electrical response of the individual sensor 32. In an example, each detector is an ammeter.

The flow cell 10" disclosed herein may be used for single molecule detection of a polymerase incorporation event (i.e., which nucleotide has been incorporated into a nascent strand). More particularly, the charge sensors 32 can monitor the dynamics of a single molecule reaction.

For single molecule detection, a template polynucleotide chain may be introduced to the flow cell 10". The template polynucleotide chain may be any sample that is to be sequenced, and may be composed of DNA, RNA, or analogs thereof (e.g., peptide nucleic acids). The source of the template (or target) polynucleotide chain can be genomic DNA, messenger RNA, or other nucleic acids from native sources.

The template polynucleotide chain may be held in place by the polymerase (one example of the enzyme 36), which is directly or indirectly attached to the nanostructure 30. The template polynucleotide chain may be introduced in a biologically stable solution, along with reagents, such as nucleotide(s) that are to be incorporated into a nascent strand formed along the template polynucleotide chain. The biologically stable solution may be any buffer suitable for polymerase base incorporation reactions, such as polymerase chain reaction (PCR) or linear amplification. As an example, a biologically stable solution may include a buffer having a pH near 7, a salt concentration above several millimolar, and $Mg^{2+}$ ions at millimolar concentration.

At least some of the nucleotide(s) that are introduced may include a base that is complementary to a target nucleic acid of the template polynucleotide chain. The nucleotide will be held in place, in part, by the polymerase that is also bound to the template polynucleotide chain. The bound nucleotide alters the signal at the charge sensor 32, which is detectable at the detector.

After a single molecule (nucleotide) is detected by the charge sensor(s) 32, it is to be understood that the flow cell 10" may be exposed to a de-patterning reagent, such as the oxidizing reagents disclosed herein. In this example, the de-patterning reagent will remove the bound nucleotide from the polymerase and will also oxidize the di-imide of the porous molecular network 14, which will detach the porous molecular network 14 from the substrate 12.

The flow cell 10" may be used again by introducing a patterning reagent (including the porous molecular network pre-assembled in solution), which forms a fresh porous molecular network 14 on the substrate 12 around the charge sensors 32, and then introducing a sample, which includes nucleotide(s) to be introduced to a next target nucleic acid of the template polynucleotide chain. The single molecule detection, de-patterning, and re-patterning may be continued for the entire template polynucleotide chain.

This flow cell 10" could also be used again in other sequencing operations with a different template polynucleotide chain.

Lid for Flow Cells

The examples shown in FIG. 2, FIG. 3B, and FIG. 6 are examples of the flow cell 10, 10', 10" without a lid bonded thereto. While not shown, the flow cells 10, 10', 10" may have the lid bonded to at least a portion of the substrate 12. The lid may be positioned on the substrate 12 so that it defines a single flow channel or multiple, fluidically separated flow channels. It is to be understood that the surface chemistry 20, 20' (either singly or as an array) is present in the flow channel(s).

With the flow cells 10, 10' (which utilize optical sensing), the lid may be any material that is transparent to an excitation light that is directed toward the surface chemistry 20. As examples, the lid may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P. With the flow cells 10" (which utilize electronic sensing), the lid may be any material, including the transparent materials or any other desired material. The lid may be bonded using any suitable technique, such as laser bonding, diffusion bonding, anodic bonding, eutectic bonding, plasma activation bonding, glass frit bonding, or others methods known in the art.

Sensing System

Figure 7:
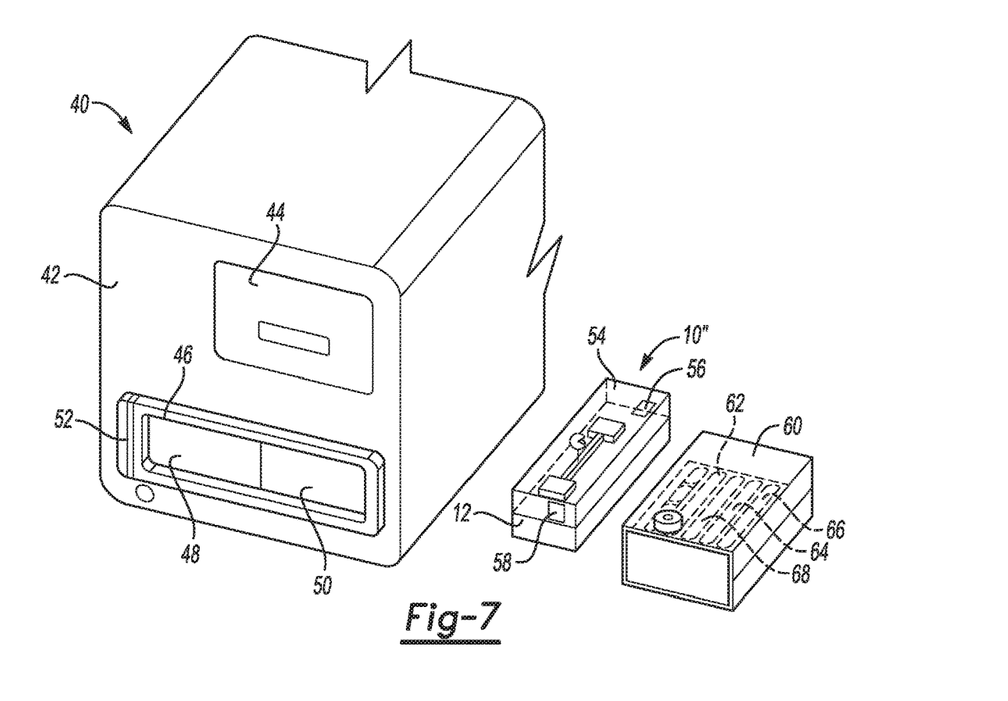
FIG. 7 is a perspective view of a portion of an example sequencing system disclosed herein.

One example of a sensing system 40 disclosed herein is shown in FIG. 7. This system 40 includes the flow cell 10" and is an electronic sensing system 40. In this example, the flow cell 10" is referred to as a removable flow cell 10", but it is to be understood that this flow cell 10" may be permanently enclosed in the system 40 or may be removable from the system 40. In the removable example, the removable flow cell 10" can be removed and replaced with a new removable flow cell 10", for example, for different sequencing operations. The sensing system 40 is one example, and it is to be understood that other configurations of the system may be used.

The example sensing system 40 is an electronic sensing system, which includes a housing 42 that contains various fixed components including, for example, electrical components, computational components, power source, fan, and the like. A screen 44 may be present, for example, on the front face of the housing 42, and may function as a graphical user interface that can provide various types of information such as operational status, status of an analytical procedure (e.g., a sequencing run) being carried out, status of data transfer to or from the device 40, instructions for use, warnings, or the like. A receptacle 46 is also present on the front face of the housing 42. The receptacle 46 may include two sections, a flow cell receptacle portion and a reagent cartridge receptacle portion. The flow cell portion of the receptacle 46 may permanently house the removable flow cell 10" or may receive (and release) the removable flow cell 10". When the flow cell portion of the receptacle 46 permanently houses the removable flow cell 10", the receptacle 46 may include a single slot 50 to receive a reagent cartridge in the reagent cartridge receptacle portion. When the flow cell portion of the receptacle 46 receives the replaceable flow cell 10", the receptacle 46 may include two slots 48, 50, one of which is to receive the removable flow cell 10" and the other of which is to receive the reagent cartridge. The slot(s) 48, 50 may have protective door(s).

The sensing system 40 may include a status indicator 52, which in this example is in the form of an indicator light on the frame of the receptacle 46. The status indicator 52 can indicate the presence or absence of a reagent cartridge and/or of a replaceable flow cell 10".

As shown, the flow cell 10" includes the substrate 12 and the lid 54. Whether permanent or replaceable, the removable flow cell 10" may also include input and output fluid ports 56, 58 that enable delivery of bulk reagents to the charge sensor(s) 32 (FIG. 5A) of the removable flow cell 10".

The sequencing system 40 may also include a reagent delivery system to selectively introduce reagent(s) to an input fluid port 56 of the removable flow cell 10", over the sensors 32, and then out of the fluid output ports 58 of the removable flow cell 10". The reagent delivery system may include tubing or other fluidics that can permanently or removably attach to the ports 56, 58. The reagent deliver system may also include tubing or other fluidics that can operatively connect to a reagent cartridge 60. The reagent deliver system may also include a pump or other suitable equipment to retrieve the reagent(s) from the reagent cartridge 60 and deliver it to the input fluid port 56 according to sequencing and de-patterning/patterning protocols (e.g., in accordance with the method described herein for using the removable flow cell 10").

The reagent cartridge 60 can provide various reagents to the removable flow cell 10". The reagent cartridge 60 includes a housing that protects various fluidic components such as reservoirs, fluidic connections, pumps, valves and the like. In an example, the reagent cartridge 60 includes a fluid storage system, which includes a de-patterning reagent receptacle 62 and a de-patterning reagent (e.g., oxidizing reagent) contained within the de-patterning reagent receptacle 62; a patterning reagent receptacle including two separate compartments 64, 66, where a first component of the patterning reagent (e.g., melamine or the analog thereof) is contained within a first of the two separate compartments 64 and where a second component of the patterning reagent (e.g., PTCDI or the analog thereof) is contained within a second of the two separate compartments 66. The reagent cartridge 60 may also include a sample compartment 68, which may include sub-compartments for a template polynucleotide chain (that is to be sequenced) and for samples including nucleotides (that are to be introduced into a nascent strand formed along the template polynucleotide chain). The reagent cartridge 60 may be programmed to release the template polynucleotide chain and sample(s) during sequencing, to release the de-patterning reagent to remove a bound nucleotide and the porous molecular network 14, and to release the patterning reagents to form a fresh porous molecular network 14. The reagent cartridge 60 may also include a mixing chamber where the patterning reagents are introduced and allowed to pre-assemble before they are introduced onto the substrate 12 of the removable flow cell 10".

Additional Notes

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Furthermore, it is to be understood that the ranges provided herein include the stated range and any value or sub-range within the stated range, as if they were explicitly recited. For example, a range represented by from 1 to 50, should be interpreted to include not only the explicitly recited limits of from 1 to 50, but also to include individual values, such as about 15, 22.5, 45, etc., and sub-ranges, such as from about 20 to about 48, etc.

While several examples have been described in detail, it is to be understood that the disclosed examples may be modified. Therefore, the foregoing description is to be considered non-limiting.

What is claimed is:

1. A flow cell, comprising:
a substrate;
a selectively removable porous molecular network on the substrate and defining exposed substrate regions, wherein the selectively removable porous molecular network is a planar supramolecular network of an amine and a di-imide; and
sequencing surface chemistry on at least some of the exposed regions, the surface chemistry including:
an activated pad selected from the group consisting of a silane or a silane derivative,
a polymer layer attached to the activated pad, wherein the polymer layer is:

wherein:
$R^1$ is H or optionally substituted alkyl;
$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
$R^5$, $R_6$ and $R_8$ are each independently selected from the group consisting of H and optionally substituted alkyl;
each of the —$(CH_2)_p$— can be optionally substituted;
p is an integer in the range of 1 to 50;
n is an integer in the range of 1 to 50,000; and
m is an integer in the range of 1 to 100,000, and
a primer attached to the polymer layer, the primer including a single stranded nucleic acid sequence that is to serve as a starting point for template amplification and cluster generation.

2. The flow cell as defined in claim 1, wherein the amine is melamine or an analog thereof and wherein the di-imide is perylene tetracarboxylic di-imide or an analog thereof.

3. A method, comprising:
applying a porous molecular network to a substrate to define a pattern of exposed substrate regions, wherein the porous molecular network is a planar supramolecular network of an amine and a di-imide;
activating the exposed substrate regions to form activated pads selected from the group consisting of a silane or a silane derivative;
removing the porous molecular network, whereby the activated pads remain intact and are separated by interstitial substrate regions;
applying a respective polymer layer to each of the activated pads, wherein the respective polymer layer is:

wherein:
$R^1$ is H or optionally substituted alkyl;
$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
$R^5$, $R_6$, and $R_8$ are each independently selected from the group consisting of H and optionally substituted alkyl;
each of the —$(CH_2)_p$— can be optionally substituted;
p is an integer in the range of 1 to 50;
n is an integer in the range of 1 to 50,000; and
m is an integer in the range of 1 to 100,000; and
grafting a primer to each of the respective polymer layers, the primer including a single stranded nucleic acid sequence that is to serve as a starting point for template amplification and cluster generation.

4. A method, comprising:
applying a porous molecular network to a substrate to define a pattern of exposed substrate regions;
activating the exposed substrate regions to form activated pads selected from the group consisting of a silane or a silane derivative;
removing the porous molecular network by exposing the porous molecular network to an oxidizing reagent, whereby the activated pads remain intact and are separated by interstitial substrate regions;
applying a respective polymer layer to each of the activated pads, wherein the polymer layer is:

wherein:
$R^1$ is H or optionally substituted alkyl;
$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;

$R^5$, $R_6$ and $R_8$ are each independently selected from the group consisting of H and optionally substituted alkyl;

each of the —$(CH_2)_p$— can be optionally substituted;

p is an integer in the range of 1 to 50;

n is an integer in the range of 1 to 50,000; and m is an integer in the range of 1 to 100,000; and grafting a primer to each of the respective polymer layers, the primer including a single stranded nucleic acid sequence that is to serve as a starting point for template amplification and cluster generation.

\* \* \* \* \*